United States Patent [19]
Ufford et al.

[11] 4,328,812
[45] May 11, 1982

[54] RING ELECTRODE FOR PACING LEAD

[75] Inventors: Keith A. Ufford, Maple Grove; Edward G. O'Neill, St. Paul, both of Minn.

[73] Assignee: Medtronic, Inc., Minneapolis, Minn.

[21] Appl. No.: 133,371

[22] Filed: Mar. 21, 1980

[51] Int. Cl.³ .............................................. A61N 1/04
[52] U.S. Cl. .................................................. 128/786
[58] Field of Search .................... 128/419 P, 784, 785, 128/786

[56] References Cited

U.S. PATENT DOCUMENTS

| | | | |
|---|---|---|---|
| 3,348,548 | 10/1967 | Chardack | 128/419 P |
| 3,749,101 | 7/1973 | Williamson | 128/419 P |
| 3,871,382 | 3/1975 | Mann | 128/419 P |
| 4,258,725 | 3/1981 | O'Neill | 128/419 P |

Primary Examiner—William E. Kamm
Attorney, Agent, or Firm—Joseph F. Breimayer; John L. Rooney; Carl A. Forest

[57] ABSTRACT

Ring electrode for a bipolar pacing lead where the ring electrode is secured to an outer coiled conductor by swaging the outer coiled conductor between the ring electrode and a swaging core where the distal end of the outer coiled conductor positions over the swaging core and into the ring electrode. The outer coiled conductor is mechanically swaged between the ring electrode and the swaging core resulting in a mechanical and electrical joint. Insulation extends over the outer ends of the ring electrode and yields a bond to the ring electrode having substantially the same outer diameter as the ring electrode.

21 Claims, 2 Drawing Figures

U.S. Patent May 11, 1982 4,328,812
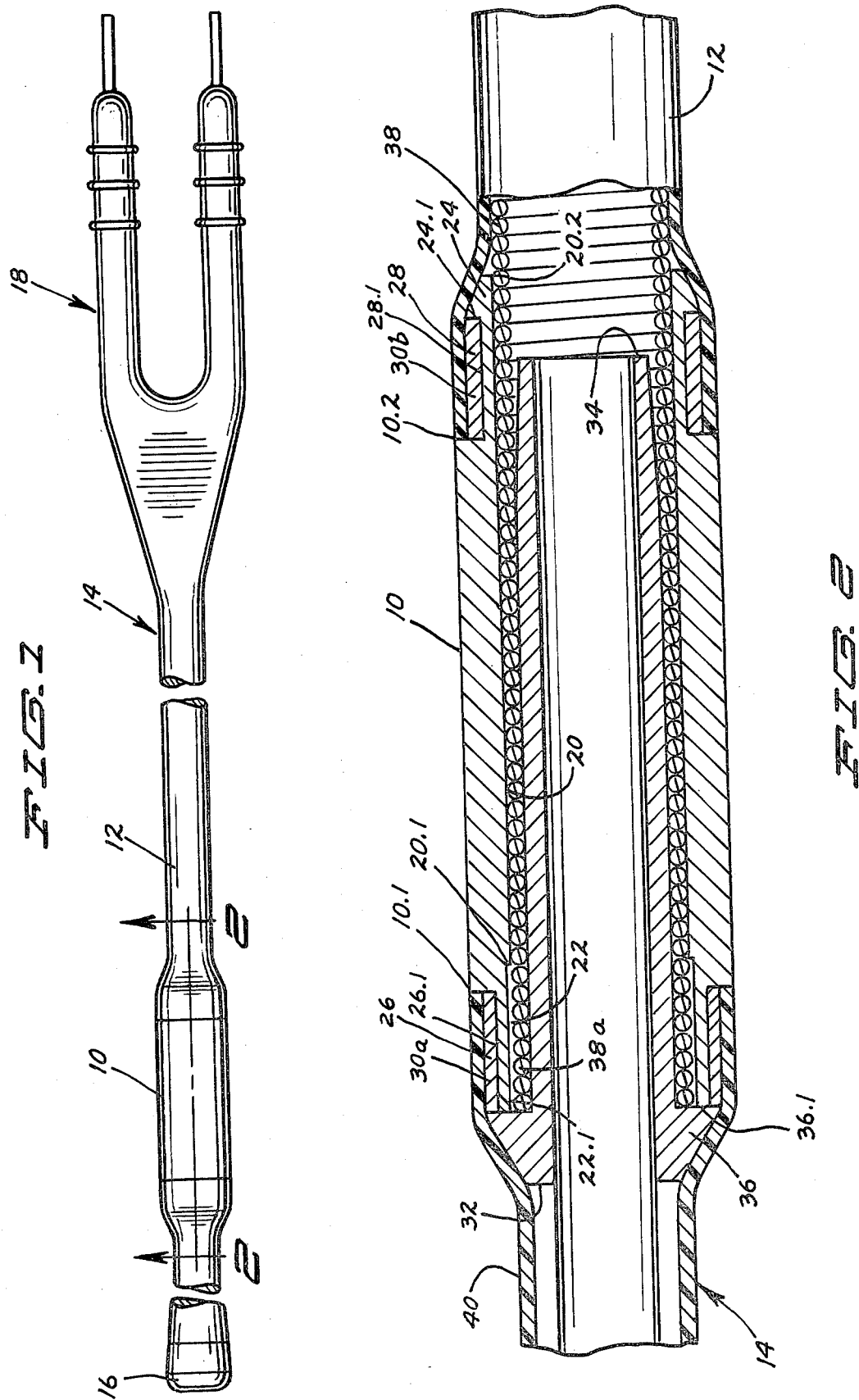

RING ELECTRODE FOR PACING LEAD

BACKGROUND OF THE INVENTION

1. Field of the Invention

The present invention relates to a surgical electrical applicator, and more importantly, pertains to a ring electrode for a bipolar pacing lead and process of making same.

2. Description of the Prior Art

Existing types of bipolar pacing leads have sometimes presented an uneven surface at the junction of the ring electrode and the insulation of the insulated coiled conductor of the bipolar pacing lead. The tensile strength of the ring electrode at the interface of the insulated coiled conductor has been considerably less than desirable when the coiled conductor has been welded to the ring electrode.

The present invention provides a ring electrode which is swaged to the outer coiled conductor of the bipolar pacing lead, and provides a smooth transition between the insulation and the ring electrode.

SUMMARY OF THE INVENTION

The present invention provides a ring electrode which is swaged to the outer conductor coil where the insulation of the coiled conductor overlaps the end and abuts up to the end of the ring electrode.

According to one embodiment of the present invention, there is provided a ring electrode on an outer coiled conductor of a bipolar pacing lead comprising an outer coiled conductor, insulation over the outer coiled conductor, a swaging core positioned internally into the distal end of the outer coiled conductor, a ring electrode, positioned externally over the distal end of the outer coiled conductor, and insulation of the outer coiled conductor abuting up to the proximal end of the ring electrode and insulation between a pacing tip at the distal end of the ring electrode and the distal end of the ring electrode abuting up to the distal end of the ring electrode whereby the outer coiled conductor is swaged between the ring electrode and the swaging core.

A significant aspect and feature of the present invention is a ring electrode on a bipolar pacing lead having enhanced tensile strength about the outer coiled conductor. The outer coiled conductor is swaged to the distal end between the ring electrode and the swaging core.

Another significant aspect and feature of the present invention is a ring electrode for a bipolar pacing lead which offers economic advantages in being easily and readily produceable with little chance for manufacturing defects providing for consistent manufacturing assembly.

A further significant aspect and feature of the present invention is a bipolar pacing lead which is flexible in the area surrounding the ring electrode.

Another significant aspect and feature of the present invention is to provide a pacing lead which is easy to pass around curves, especially in veins.

Another significant aspect and feature of the present invention is a pacing lead including a ring electrode and a bipolar pacing lead and having enhanced tensile strength about the outer coiled conductor at the ring electrode. The coiled conductor is swaged between the ring electrode and the swaging core thereby providing a smooth surface on the outer insulated surface of the pacing lead. The smooth outer surface is particularly desirable and provides for easy passage of the bipolar pacing lead through veins of the patient's body and lead insertion devices, and further minimizes thrombus formation.

Having thus described one embodiment of the present invention, it is an objective hereof to provide a ring electrode for pacing lead, especially for urethane pacing leads, having a smooth surface between the ring electrode and the lead body, and offering utmost flexibility at the interface junction of the ring electrode and the pacing lead.

BRIEF DESCRIPTION OF THE DRAWING

Other objects and many of the attendant advantages of this invention will be readily appreciated as the same becomes better understood by reference to the following detailed description when considered in connection with the accompanying drawing, in which like reference numerals designate like parts through the FIGURES thereof and wherein:

FIG. 1 illustrates a plan view of a ring electrode over a section of bipolar pacing lead, the present invention; and FIG. 2 illustrates a cross-sectional view taken along line 2—2 of FIG. 1.

DESCRIPTION OF THE PREFERRED EMBODIMENT

FIG. 1, which illustrates a plan view of a ring electrode 10 of the present invention, shows a ring electrode 10 positioned about insulation 12 of a coaxial bipolar pacing lead 14 which includes a pacing tip electrode 16 at a distal end and terminal pins 18 at the proximal end of the pacing lead 14.

FIG. 2, which illustrates a cross-sectional view taken along line 2—2 of FIG. 1, shows the ring electrode 10 on the pacing lead 14 adjacent the distal end where the outer diameter of the ring electrode 10 is slightly larger than the outer diameter of the insulation 12 of the pacing lead 14. The ring electrode 10 can be platinum, platinum-iridium, or other like material. The insulation 12 of the pacing lead 14 surrounds outer coiled conductor 38 which can be multi-filar such as quadrafilar nickel alloy coiled conductor commonly referred to as MP35N by way of example and for purposes of illustration only, and which can be manufactured under the Drawn-Brazed-Stranded (DBS) process. The insulation 12 can be urethane, polyether urethane elastomer or other like material as now used for insulating coiled conductor 38. The pacing inner coiled conductor is not illustrated for purposes of clarity in the drawing and for purposes of brevity in the specification.

The ring electrode 10 includes an outer diameter which provides for pacing from distal outer end 10.1 to proximal outer end 10.2, an inner diameter 20 from distal inner end 20.1 to proximal inner end 20.2, and a slightly elongated larger inner coil relief channel 22 which provides for coil relief from distal inner end 22.1 of channel 22 to distal inner end 20.1 of internal diameter 20. A hook 24 is provided adjacent the proximal inner end 20.2. External longitudinal circular channel 26, formed by a smaller outer diameter 26.1, and external channel 28, formed by a small diameter outer diameter 28.1 and the hook 24, are at each end of the ring electrode 10 providing for bands of tubing in the channels as now described in detail. Distal and proximal bands of tubing 30a and 30b respectively such as urethane or other like material and which can be analogized to rubber bands, snap in and engage within the external channels 26 and 28 respectively for receiving insulation as later described in detail. A swaging core 32 includes a slightly tapered proximal end 34 and a distal hook end 36 reciprocal in structure to the hook end 24 of the ring electrode 10 including an outer diameter less than the inner diameter of the coiled conductor 38 and of the same or like material as the ring electrode 10.

PREFERRED MODE OF OPERATION

The process for securing the ring electrode 10 to the distal end of an outer coaxial coiled conductor 38 comprises the steps of positioning urethane bands 30a and 30b in the channels 26 and 28 respectively, sliding the ring electrode 10 over the coiled conductor 38 adjacent the distal end of the outer coiled conductor 38, inserting the swaging core 32 having the tapered end 34 so that a hook edge 36.1 abuts up against the end winding of the coiled conductor 38 and forcing the ring electrode 10 distal end to the hook edge 36.1 of the swaging core 32 swaging the coiled conductor 38 between the ring electrode 10 and the swaging core 32 therebetween, possibly with the aid of an internal mandrel having substantially the same inner diameter as swaging core 32. The coil relief channel 22 takes up any extra slack of the distal end of the outer coiled conductor 38. Insulation 12 is then threaded over the outer coiled conductor 38 and bonded to band 30b. Subsequent steps can include the threading of a coaxial inner insulated coiled conductor not illustrated in the figures for purposes of clarity in the drawing through the outer coiled conductor 38, through the swaging core 32, and bonding of insulation 40 from the pacing tip electrode 16 over the band 30a to abut up against the distal outer end 10.1. The ends 10.1 and 10.2 of the ring electrode 10 having the insulation over the bands 30a and 30b in the valleys 26 and 28 assume substantially the same outer diameter as the outer diameter of the ring electrode 10 which is slightly larger than the diameter of the insulation 12. The hooks 24 and 36 and hook edges 24.1 and 36.1 serve to retain the insulation 12 and 40 over the pacing tip electrode 16 in position in addition to providing outer ends for the channels 26 and 28 respectively and abutment between the ring electrode 10 and the swaging core 32. A plurality of tines not illustrated in the figure can extend from the insulation 40 about the pacing tip electrode 16.

The mechanical joint resulting by the crimping and swaging of the coil conductor 38 between elements 10 and 32 can be referred to as a mechanical weld which assumes mechanical and electrical connection of the ring electrode 10 to the coiled conductor 38 about the swaging core 32.

The resultant pacing lead 14 includes a ring electrode 10 which provides for a smooth outer surface for easy lead passage through veins and a lead introducer as utilized. The ring electrode 10 provides flexibility in the area of the ring electrode 10 on the pacing lead 14, provides easy passage of the pacing lead 14 around curves, and has a tensile strength at the ring electrode 10 substantially equal that of the insulation 12 utilized over the coiled conductor 38.

Alternative embodiments of the ring electrode for a pacing lead for forseeable in light of the above specification. One embodiment is a body-implantable lead for pacing, sensing, stimulating or like medical applications and includes electrode applicator structure at the end of the lead where the electrode application includes the swaging core having a rounded forward portion, the distal end of the conductor, and a cylindrical tubular conductor member in lieu of the ring electrode structure and including only one circumferential channel at the proximal end. Ring electrode can include the structure of a cylindrical tubular conductive member having an outer cylindrical surface. Also, the ring electrode can include only one channel for a band of insulation, either distal or proximal, or in the alternative, one of the bands can be used for bonding insulation to one end of the electrode.

Various modifications can be made to the ring electrode 10 of the pacing lead of the present invention without departing from the apparent scope thereof.

Having thus described the invention, there is claimed as new and desired to be secured by Letters Patent:

1. A body-implantable lead comprising a length of conductor having proximal and distal ends; connector means coupled to said proximal end of said conductor; electrode means coupled to said distal end of the conductor and tubular insulating means surrounding said conductor between exposed portions of said electrode means and said connector means; wherein said electrode means further comprises a cylindrical, tubular conductor member having an outer cylindrical surface; and circumferential channel at an end of said member recessed into said outer cylindrical surface to a predetermined depth; a hook incuding a hook edge on a proximal end of said member for engaging said tubular insulating means; an elastic band of insulating material fitting within said circumferential channel; and means for bonding a terminal portion of said insulating means to said elastic band, the combined thickness of said elastic band, said bonding means and said insulation means being equal to said predetermined depth whereby a smooth uninterrupted surface is presented at the interface of said electrode means and said insulating means.

2. Body implantable lead for electrical applications having an outer coiled conductor covered with a sheath of insulation and including an electrode adjacent a distal end of said lead, said electrode comprising:

cylindrical tubular conductive member having an outer cylindrical surface, and having a hook including a hook edge on a proximal end of said member for engaging said sheath of insulation disposed over a distal end of said outer coiled conductor of said body implantable lead and a swaging core disposed in the distal end internal of said outer coiled conductor whereby said member is disposed over said distal end of said outer coiled conductor to said swaging core thereby engaging said outer coiled conductor between said member and said swaging core and providing electrical continuity between said outer coiled conductor and said member.

3. Body implantable lead of claim 2 comprising a longitudinal circular channel in a proximal end of said member and a proximal end band of insulation disposed in said channel whereby said insulation of said outer conductor is bonded to said proximal band of insulation.

4. Body implantable lead of claim 3 wherein said swaging core means comprises a hook at distal end whereby said hook engages against said distal end of said member.

5. Body implantable lead of claim 2 comprising an inner coiled relief channel including an elongated diameter slightly larger than the internal diameter of said member whereby said coiled relief channel accepts said distal end of said outer coiled conductor.

6. Body implantable lead of claim 2 wherein said swaging core means comprises longitudinal circumferential member including a slightly tapered end.

7. Body implantable lead of claim 2 wherein said insulation is urethane.

8. Body implantable lead of claim 2 wherein said insulation is polyether urethane elastomer.

9. Pacing lead including a ring electrode, said pacing lead comprising:
   a. coiled conductors including electrodes at distal ends of at least one inner coiled conductor and terminal pins at a proximal end of said inner coiled conductor;
   b. insulation over each of said coiled conductors; and
   c. ring electrode having a hook with a hook edge for engaging said insulation disposed over a distal end of a first coiled conductor and a swaging core disposed in the distal end internal of said first coiled conductor whereby said ring electrode is pulled over said distal end of said first coiled conductor to said swaging core thereby swaging said first coiled conductor between said ring electrode and said swaging core and providing electrical continuity between said first coiled conductor and said ring electrode.

10. Pacing lead of claim 9 comprising a longitudinal circular channel in each end of said ring electrode and distal and proximal end bands of insulation disposed in each of said channels for bonding said insulation of said conductor to said proximal band of insulation and to said distal band.

11. Pacing lead of claim 10 wherein said swaging core means comprises a hook at distal end whereby said hook acting in combination with said ring electrode thereby forms a channel engaging said distal end band.

12. Pacing lead of claim 9 comprising an inner coiled relief channel including an elongated diameter slightly larger than the internal diameter of said ring electrode whereby said coiled relief channel accepts said distal end of said coiled conductor.

13. Pacing lead of claim 9 wherein said swaging core means comprises longitudinal circumferential member including a slightly tapered end.

14. Pacing lead of claim 9 wherein said insulation is urethane.

15. Pacing lead of claim 9 wherein said insulation is polyether urethane elastomer.

16. A body implantable lead comprising:
    a coiled conductor having a lumen, a proximal end, and a distal end;
    a sheath of body compatible insulating material covering said coiled conductor;
    an electrode electrically coupled to said coiled conductor; and
    hook edge means coupled to said electrode for frictionally engaging said sheath of body compatible insulating material.

17. A body implantable lead according to claim 16 wherein said first frictionally engaging means further comprises a channel intermediate said electrode and said hook and a band of said body compatible insulating material disposed within said channel.

18. A body implantable lead according to claim 16 or 17 further comprising:
    a swaging core located within said lumen and frictionally engaging said coiled conductor.

19. A body implantable lead according to claim 18 further comprising:
    second means coupled to said swaging core for frictionally engaging said sheath of body compatible insulating material.

20. A body implantable lead according to claim 19 wherein said second frictionally engaging means further comprises a hook.

21. A body implantable lead according to claim 20 wherein said second frictionally engaging means further comprises a channel intermediate said electrode and said hook and a band of said body compatible insulating material disposed within said channel.

* * * * *

UNITED STATES PATENT AND TRADEMARK OFFICE
CERTIFICATE OF CORRECTION

PATENT NO. : 4,328,812
DATED : May 11, 1982
INVENTOR(S) : UFFORD et al

It is certified that error appears in the above—identified patent and that said Letters Patent are hereby corrected as shown below:

Column 3,
    Line 65, "for" should be --are--;

Claim 1,
    Line 27, "and" should be --a--.

Signed and Sealed this

Twenty-sixth Day of October 1982

[SEAL]

Attest:

Attesting Officer

GERALD J. MOSSINGHOFF

Commissioner of Patents and Trademarks